(12) United States Patent
Cole et al.

(10) Patent No.: US 10,265,466 B2
(45) Date of Patent: Apr. 23, 2019

(54) FLUID INFUSION DEVICE

(71) Applicant: Becton, Dickinson and Company, Franklin Lakes, NJ (US)

(72) Inventors: Russell Cole, River Vale, NJ (US); Michael Creighton, Hatboro, PA (US); Alyssa Jackson, Philadelphia, PA (US); Arthur Klotz, Willow Grove, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 39 days.

(21) Appl. No.: 15/301,335

(22) PCT Filed: Apr. 23, 2015

(86) PCT No.: PCT/US2015/027363
§ 371 (c)(1),
(2) Date: Sep. 30, 2016

(87) PCT Pub. No.: WO2015/164649
PCT Pub. Date: Oct. 29, 2015

(65) Prior Publication Data
US 2017/0182243 A1    Jun. 29, 2017

Related U.S. Application Data

(60) Provisional application No. 61/983,972, filed on Apr. 24, 2014.

(51) Int. Cl.
*A61M 5/158* (2006.01)
*A61M 5/142* (2006.01)
(Continued)

(52) U.S. Cl.
CPC ........ *A61M 5/158* (2013.01); *A61M 5/14248* (2013.01); *A61M 5/16877* (2013.01);
(Continued)

(58) Field of Classification Search
CPC .. A61M 5/158; A61M 5/172; A61M 5/16877; A61M 5/14248;
(Continued)

(56) References Cited

U.S. PATENT DOCUMENTS 6,016,595 A    1/2000  Dysarz
2007/0185516 A1*  8/2007  Schosnig ......... A61B 5/150022
                                                    606/181

(Continued)

FOREIGN PATENT DOCUMENTS

JP    2010-501281 A    1/2010
JP    2016-523123 A    8/2016

*Primary Examiner* — Amber R Stiles
(74) *Attorney, Agent, or Firm* — Dickinson Wright, PLLC

(57) ABSTRACT

A fluid infusion device is provided with a cannula spring which functions as an introducer needle, a retraction return spring, and a fluid path. A hollow cannula tubing is wound, bent and sharpened into a shape which allows it to operate as an introducer needle, retraction spring and fluid path in an infusion device. A button is used to insert the introducer needle portion of the cannula spring and a soft catheter, and once the introducer needle portion and catheter have been fully inserted, an engagement between the button and post of the base of the infusion device releases the cannula spring such that the introducer needle portion of the cannula spring automatically retracts, leaving the catheter in the body. An end of the introducer needle portion of the cannula spring remains in fluid communication with the catheter in the body to provide an uninterrupted fluid path.

9 Claims, 10 Drawing Sheets

(51) Int. Cl.
*A61M 5/168* (2006.01)
*A61M 5/172* (2006.01)

(52) U.S. Cl.
CPC ... *A61M 5/172* (2013.01); *A61M 2005/14252* (2013.01); *A61M 2005/1585* (2013.01); *A61M 2205/3337* (2013.01); *A61M 2205/3386* (2013.01); *A61M 2205/3592* (2013.01); *A61M 2205/8206* (2013.01)

(58) Field of Classification Search
CPC .. A61M 2005/1585; A61M 2205/3337; A61M 2205/3386; A61M 2205/3592; A61M 2005/14252; A61M 2205/8206
See application file for complete search history.

(56) References Cited

U.S. PATENT DOCUMENTS

| | | | |
|---|---|---|---|
| 2008/0051714 A1* | 2/2008 | Moberg | A61M 5/1413 604/135 |
| 2010/0217105 A1* | 8/2010 | Yodfat | A61B 5/14503 600/365 |
| 2010/0286615 A1 | 11/2010 | Gyrn et al. | |
| 2011/0054285 A1 | 3/2011 | Searle et al. | |
| 2011/0054390 A1 | 3/2011 | Searle et al. | |
| 2012/0316506 A1 | 12/2012 | Sonderegger et al. | |
| 2013/0204191 A1 | 8/2013 | Cindrich et al. | |
| 2014/0031793 A1 | 1/2014 | Constantineau et al. | |
| 2016/0082182 A1* | 3/2016 | Gregory | A61M 5/14526 604/150 |

* cited by examiner

FLUID INFUSION DEVICE

CROSS-REFERENCE TO RELATED APPLICATION

This application claims the benefit under 35 U.S.C. § 119(e) of U.S. Provisional Application No. 61/983,972, filed on Apr. 24, 2014 in the U.S. Patent and Trademark Office, the contents of which are incorporated herein by reference.

FIELD OF THE INVENTION

The present invention relates generally to medical infusion systems, such as a fluid infusion device, where a piece of hollow cannula tubing is wound, bent and sharpened into a shape which allows it to operate as an introducer needle, retraction spring and fluid path in an infusion device. A button of the infusion device is used to insert the introducer needle portion of the cannula spring and a soft catheter, and once the introducer needle portion and catheter have been fully inserted, an engagement releases the cannula spring such that the introducer needle portion of the cannula spring automatically retracts, leaving the catheter in the body of the user. An end of the introducer needle portion of the cannula spring remains in the inserted catheter to provide an uninterrupted fluid path.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which, infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

In order to minimize the height of the insertion mechanism, some conventional insertion mechanisms are configured to insert the cannula at an acute angle from the surface of the skin, e.g. 30-45 degrees. However, it may be preferable to insert the cannula perpendicular or close to the perpendicular from the surface of the skin, since this would require the minimum length of cannula insertion. In other words, with the minimum length of cannula being inserted into the user's skin, the user can experience greater comfort and fewer complications, such as premature kinking of the cannula. But one problem with configuring the insertion mechanism to insert the cannula perpendicular to the surface of the skin is that this may increase the overall height of the insertion mechanism, and therefore of the patch pump itself.

Accordingly, a need exists for an improved insertion mechanism for use in a limited space environment, such as in the patch pump, that can cost-effectively insert a cannula vertically or close to perpendicularly into the surface of a user's skin, while minimizing or reducing its height, in order to reduce the overall height of the device the insertion mechanism is incorporated into, such as a patch pump.

SUMMARY OF THE INVENTION

An object of the present invention is to substantially address the above and other concerns, and provide advanced, improved, and novel components and elements of an infusion device that facilitates insertion of the in-dwelling or soft catheter and if required, retract the introducer needle, while reducing the number of components required for the construction and use of the infusion device.

Another object of the present invention is to provide an infusion device that can utilize components with one or more shared technical features such that each component can serve multiple functions.

Another object of the present invention is to provide an infusion device that can utilize components which serve multiple functions, such that the part count of the exemplary embodiments is lowered and which serves to keep part production costs low and simplify device assembly.

Another object of the present invention is to provide an infusion device that can utilize a cannula spring which functions as an introducer needle, retraction spring, and fluid path.

Another object of the present invention is to provide an infusion device that can utilize an introducer needle, spring, and fluid path as all inherently part of a cannula spring.

These and other objects are substantially achieved by providing an infusion device with a cannula spring which functions as at least an introducer needle, spring and fluid path. A single piece of hollow cannula tubing is wound, bent and sharpened into a shape which allows it to operate as an introducer needle, retraction spring and fluid path in an infusion device. A button of the infusion device is used to insert the introducer needle portion of the cannula spring and a soft catheter, and once the introducer needle portion and catheter have been fully inserted, an engagement between the button and the base of the infusion device releases the cannula spring such that the introducer needle portion of the cannula spring automatically retracts, leaving the catheter in the body of the user. An end of the introducer needle portion of the cannula spring remains in the inserted catheter to provide an uninterrupted fluid path.

Additional and/or other aspects and advantages of the present invention will be set for in the description that follows, or will be apparent from the description, or may be learned by the practice of the invention. The present invention may comprise a method or apparatus or system having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

Figure 1A:
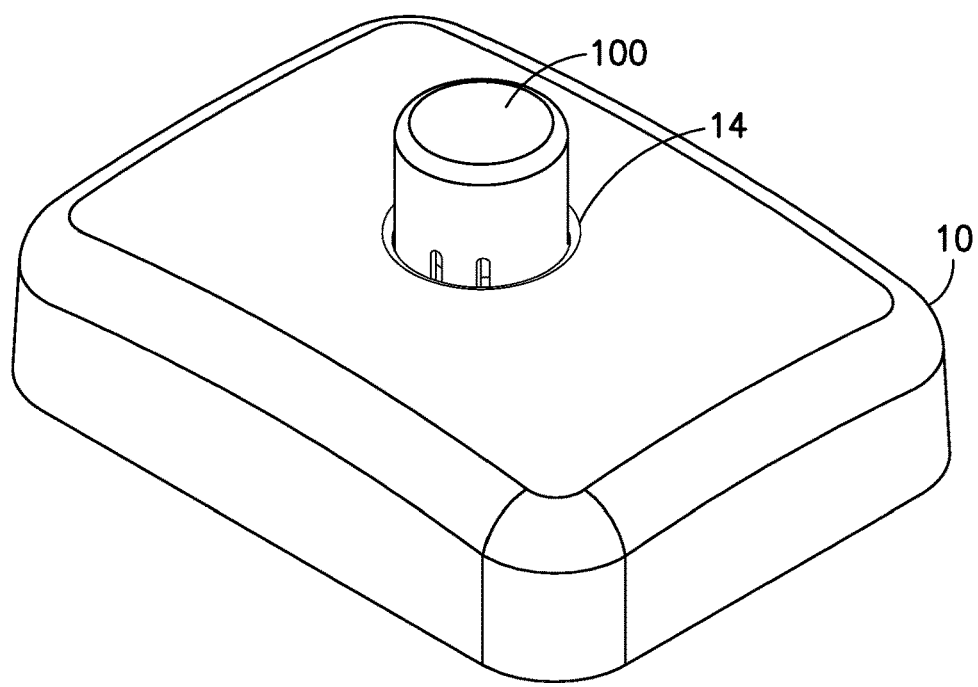
FIG. 1A is a perspective view of an exemplary infusion device prior to activation in accordance with an embodiment of the present invention.

The exemplary embodiments of the present invention described below provide novel means of providing one or more infusion device elements that are configured to share functions, thereby reducing the overall number of components required for the construction and use of the infusion device. In one embodiment, the present invention is directed to an infusion device that provides a cannula spring that is configured to function as an introducer needle, retraction spring, and fluid communication path, thereby reducing the overall number of components required for the construction and use of the infusion device.

In an exemplary embodiment, an infusion device utilizes a single piece of cannula tubing that is wound, bent and sharpened into a shape which allows it to operate as an introducer needle, retraction spring and fluid path. The cannula spring is configured to operate as an introducer needle using a sharpened introducer needle portion and operate as a spring using a coiled spring portion. For illustration purposes, the coiled spring portion in the following discussion is presented as a retraction spring, but is not limited thereto. The retraction spring portion works with other components in the set in order to insert the introducer needle portion along with a catheter into a body of the user. The introducer needle portion is then automatically retracted from the body using the coiled spring portion and the catheter is left in place. A distal end of the introducer needle portion remains in the inserted catheter in order to provide an uninterrupted fluid path with the catheter.

Since the introducer needle, retraction spring and fluid path are all inherently part of the single piece of cannula tubing, no flexible tubing is required. Flexible tubing is used in other designs so the fluid path can move along with the motion of the introducer needle and/or catheter. Such flexible tubing requires significant space within the infusion device to keep it from being pinched or kinked. Such flexible tubing can also be difficult to handle during production because it lacks any rigid shape. Further, since the introducer needle, retraction spring and fluid path are all inherently part of the single piece of cannula tubing, the part count of the device is lower and the overall size of the device is smaller than conventional devices. Accordingly, exemplary embodiments of the present invention keep part production costs low, as well as simplify assembly of the infusion device.

The exemplary embodiments of the present invention are possible due to one or more shared technical features of the elements therein. For example, cannulae of an infusion device are typically constructed using metal or plastic, such as 304 stainless steel. In some cases, such materials can also be used to construct springs and fluid paths. For example, a diameter of such cannulae can be substantially the same as a diameter of spring wire, such as that used for insertion, retraction, or safety springs in an infusion device. In one example, an operational retraction spring can be formed from a single continuous piece of steel tubing with diameter of about 0.0103 inches (0.26 mm), which shares the same diameter as a 31G steel cannula. 31 G is the most common gauge for steel in-dwelling patient cannula, such as those available from V-Go™ and Orbit™. An exemplary retraction spring formed from the steel tubing with a diameter of about 0.00103 inches (0.26 mm) in this manner exerts a force of about 0.35 lbs (1.56 N) at the beginning of retraction and about 0.17 lbs (0.76 N) at the end of the retraction. The spring force is proportional to the inverse of the polar moment of inertia which, for an annulus, is noted below in Equation (1).

$$\pi/2(\text{outer radius}^4 - \text{inner radius}^4) \qquad \text{Equation (1)}$$

In the above Equation (1), the outer diameter to the fourth power is by far the dominant term. If a regular wall thickness cannula, that is, a cannula with a wall thickness of about 0.003 inches (0.076 mm), is used to make the retraction spring, the spring force would only drop by about 6% compared to the retraction spring formed from the steel tubing with a diameter of about 0.00103 inches (0.26 mm). This reduced spring force would still give the necessary retraction force. This indicates that a hollow cannula can be used to construct a retraction spring with the same geometry, and exhibits very similar behavior. The advantage of doing so with an infusion device is that the device then requires fewer parts and would result in a smaller mechanism.

Accordingly, exemplary embodiments of the present invention utilize a cannula spring that is made of a single piece of tubing in which one end of the tubing is used as an introducer needle portion and the other end of the tubing is used to connect to a fluid path, and a middle portion of the tubing is coiled to form a spring portion. For discussion purposes, the spring portion is used as a retraction spring, but embodiments are not limited thereto. In other embodiments, the spring portion is used as an insertion spring or safety spring. Further, for discussion purposes, a single piece of steel cannula tubing is used, but embodiments are not limited thereto and in other embodiments, plastic tubing can be used.

The retraction spring portion works with other components in the infusion device in order to insert the introducer needle portion along with a catheter into the body of the user. The introducer needle portion is then retracted from the body using the retraction spring portion, and the catheter is left in place. A distal end of the introducer needle portion remains in the inserted catheter in order to provide an uninterrupted fluid path with the catheter.

Figure 1B:
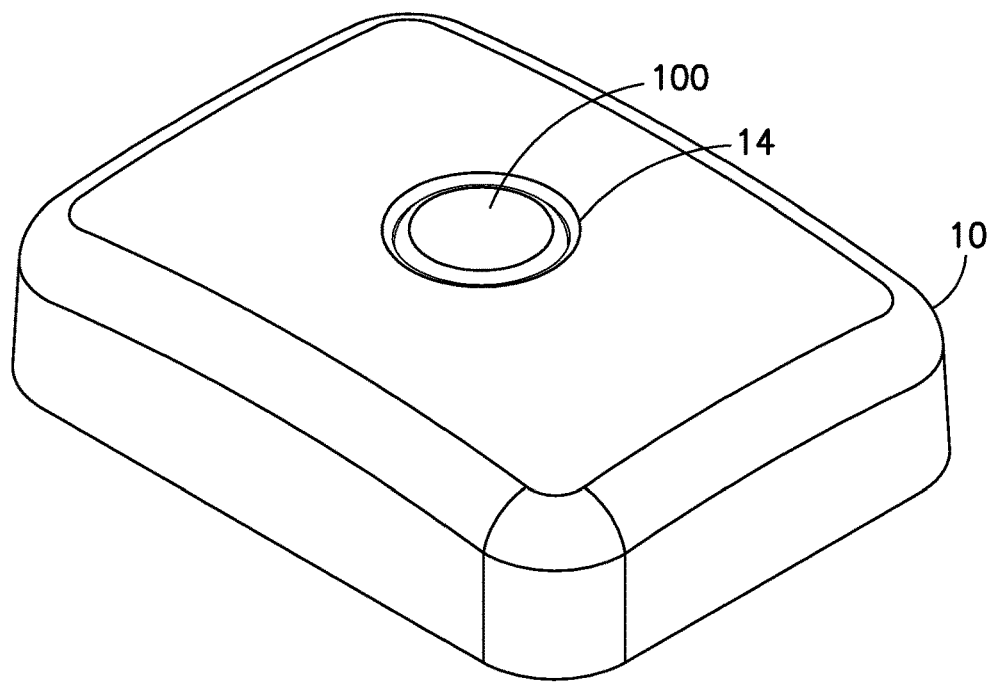
FIG. 1B is a perspective view of the exemplary infusion device of FIG. 1A after activation in accordance with an embodiment of the present invention.

FIGS. 1A and 1B show an exemplary infusion device in pre-activation and post-activation states. FIG. 1A is a perspective view of an exemplary infusion device prior to activation, and FIG. 1B is a perspective view of the exemplary infusion device of FIG. 1A after activation in accordance with an embodiment of the present invention.

Figure 2:
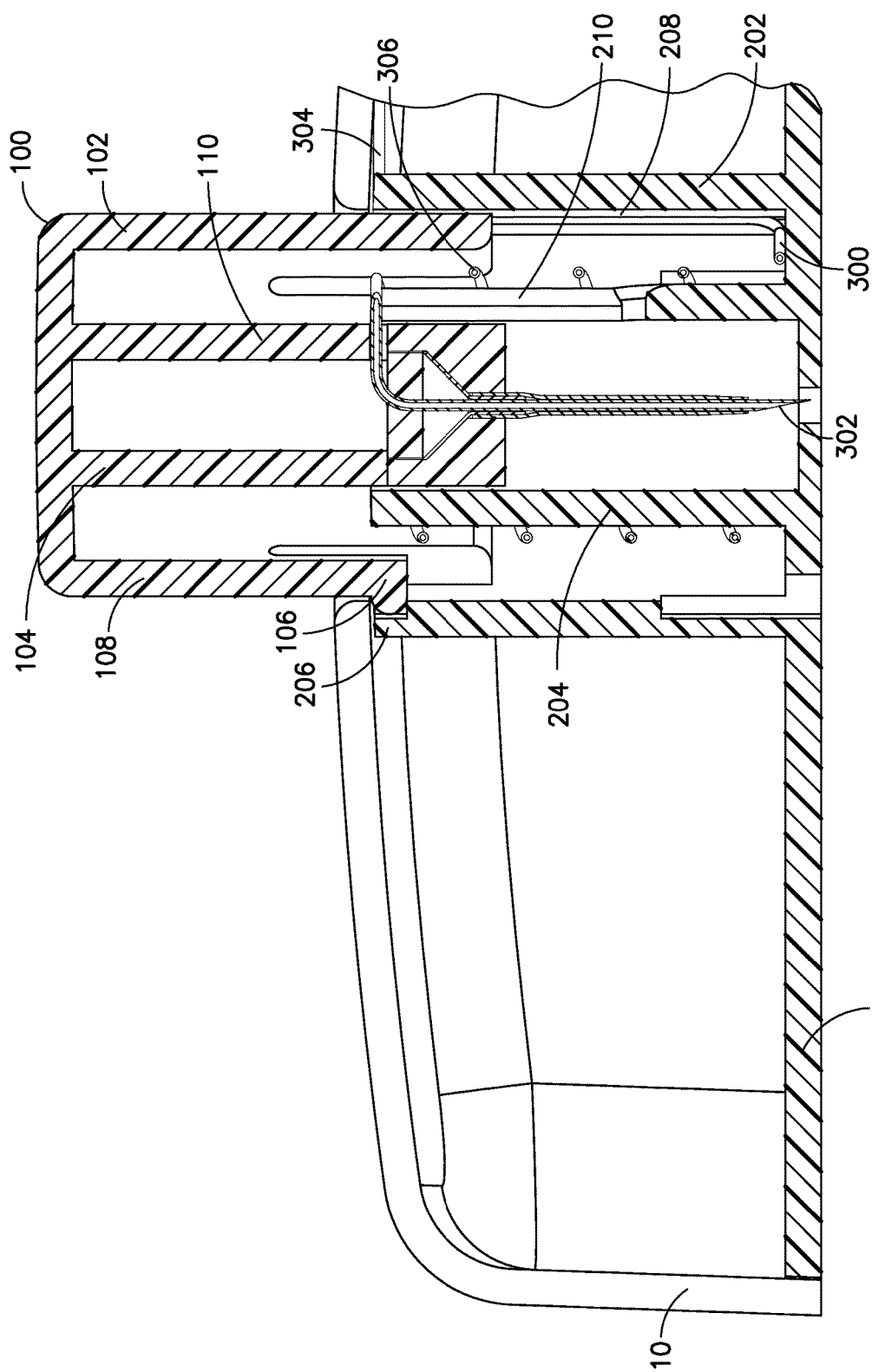
FIG. 2 is an enlarged cross-sectional view of the exemplary infusion device of FIG. 1A before activation in accordance with an embodiment of the present invention.

In FIGS. 1A and 1B, an infusion device housing 10 is shown having an opening 14 through a top surface from which a user-accessible, and user-acutatable button 100 slidably extends. As illustrated in FIG. 2, the housing is secured to an infusion device base 200, which includes a first post 202 and second post 204 to slidably receive the button 100.

The button 100 includes a first projection 102 and a second projection 104. The first projection 102 forms an outer surface of the button 100 and is slidably received by the first post 202 of the base 200. The second projection 104 extends within the first projection 102 and is slidably received by the second post 204 of the base 200. Each of the posts of the base, and projections of the button, can be substantially cylindrical but embodiments are not limited thereto. Further, each can be provided with grooves, slots and openings permitting use of the cannula spring.

Figure 3:
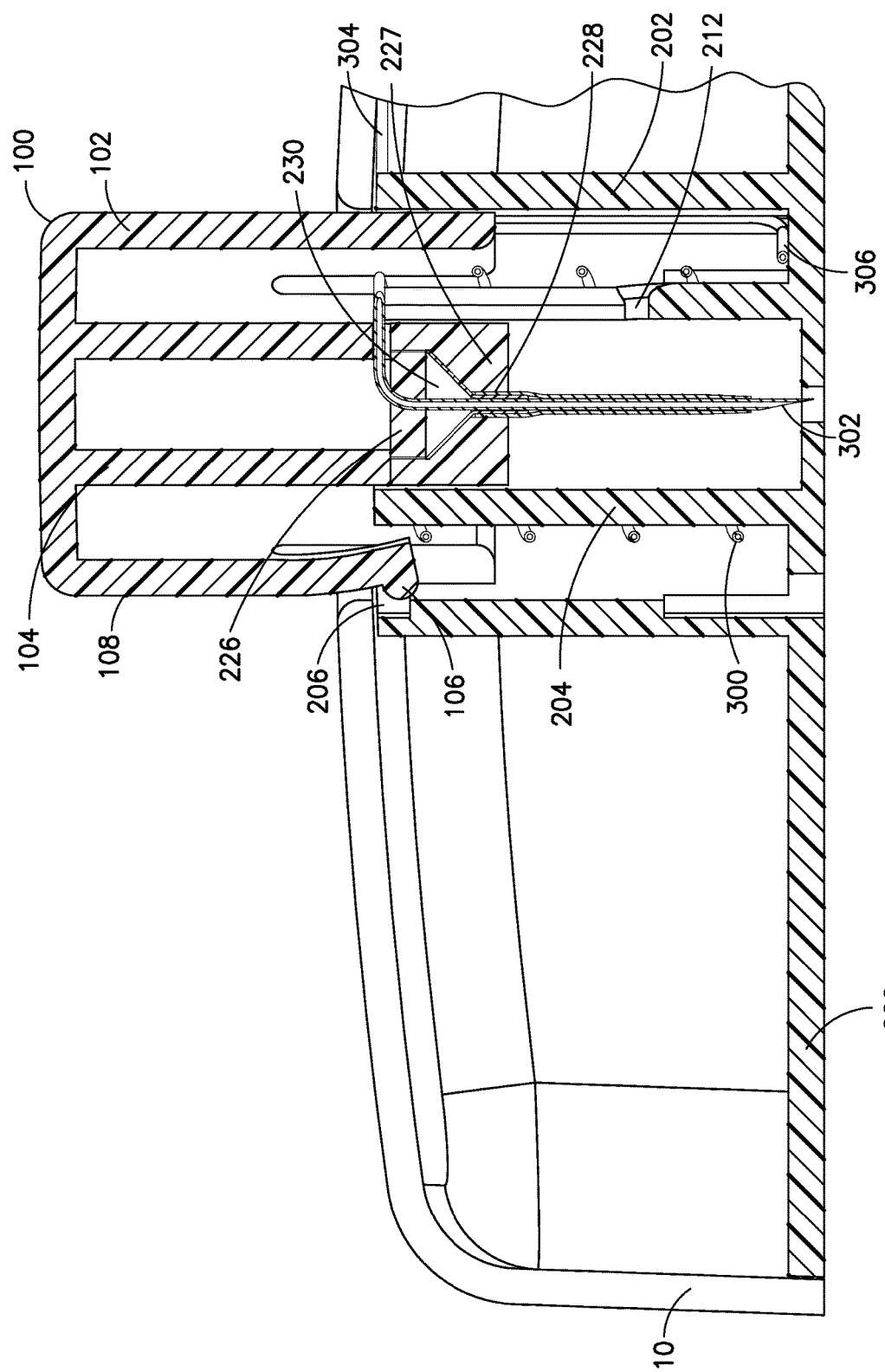
FIG. 3 is an enlarged cross-sectional view of the exemplary infusion device at the beginning of activation in accordance with an embodiment of the present invention.

The second post 204 of the base 200 slidably contains a septum 226 and therein a catheter 228 and catheter securing wedge 230 as shown in FIG. 3. Catheter 228 is attached to the wedge 230 and the septum 226 is inserted into the wedge 230 and contained in a catheter holder 227. As described in greater detail below, the second projection 104 of the button 100 is used to slidably move the septum 226, catheter 228 and catheter securing wedge 230 during activation. Other features and functions of the infusion device that are well-known to those skilled in the art are omitted from the figures and discussion for clarity.

The infusion device of FIGS. 1A and 1B is activated by pressing downward on the button 100 that protrudes from the top of the housing 10. In order to ensure that the button 100 is pressed downward with a proper force, speed, smoothness and angle, a set of detents 106, 206 as shown in FIG. 2 are used to keep the button 100 in the up position until the proper activation force, speed, smoothness and angle have been applied. FIG. 2 is an enlarged cross-sectional view of the exemplary infusion device of FIG. 1A before activation in accordance with an embodiment of the present invention and illustrates detents 106, 206. As shown in FIG. 2, the detents 106, 206 include a projecting detent 106 disposed upon an outer circumference of the first projection 102 of the button 100. The rounded, projecting detent 106 is disposed at an end of a deflectable member 108 of the button 100 and, in an up position, is releasably captured by a stepped detent 206 of the first post 202 of the base 200. The projecting detent 106 and thereby, the button 100, is releasably held in the up and extended position by the engagement between the projecting detent 106 and the stepped detent 206.

Once the desired amount of activation force, speed, smoothness and angle has been applied to the button 100, the detents 106, 206 resiliently deflect, releasing the engagement between the projecting detent 106 and the stepped detent 206 allowing the button 100 to be pressed downward as shown in FIG. 3. FIG. 3 is an enlarged cross-sectional view of the exemplary infusion device at the beginning of activation in accordance with an embodiment of the present invention. Specifically, once the desired amount of activation force, speed, smoothness and angle has been applied to the button 100, the rounded detent 106 and member 108 are deflected and are released from the engagement with the stepped detent 206 of the post 202 of the base 200. The button 100 is then free to be pressed downward against the resistance of the deflected detent 206 and member 208 resiliently urged into contact with the inner diameter of the post 202 of the base 200.

The release of the projecting detent 106 from the stepped detent 206 is configured to occur once a desired amount of activation force has been applied to the button 100. Since the button 100 is releasably held in the up and extended position by the engagement between the projecting detent 106 and the stepped detent 206, the force applied to the button 100 by the user steadily increases for some period of time prior to release of the projecting detent 106 from the stepped detent 206. Upon sudden release of the projecting detent 106 from the stepped detent 206, the force has reached a desired value and therefore, the button 100 is accelerated downward due to the sudden freedom to travel and the desired force applied to the button at the time of release and maintained thereafter. Such release ensures that a desired amount of downward force, speed, smoothness and angle has been applied by the user. Such activation substantially eliminates variations in the user force applied, speed, smoothness and angle thereof, and reduces insertion failure and/or discomfort to the user.

FIG. 2 also shows an exemplary cannula spring 300 that is made of a single piece of steel cannula tubing in which one end 302 of the tubing is used as an introducer needle portion and the other end 304 of the tubing is used to connect to a fluid path. A middle portion 306 of the tubing is coiled to form a spring portion. For discussion purposes, the spring portion 306 of the tubing is used as a retraction spring, but embodiments are not limited thereto. In other embodiments, the spring portion can be used as an insertion spring or safety spring.

An exemplary path of the cannula spring 300 as shown in FIG. 2 will now be described. The end 304 of the cannula spring 300 is used to connect to a fluid path, including any of a reservoir (not shown) within the housing 10 or to an external reservoir via one or more tube set couplings (not shown). The end 304 of the cannula spring 300 passes through the first post 202 of the base 200, preferably at a portion at or near the interface between the first post 202 and the housing 10 of the infusion device. In doing so, the end 304 of the cannula spring 300 is used to connect to a fluid path and does not move during the insertion and retraction process.

The cannula spring 300 is then disposed along a groove or slot 208 in the first post 202 of the base 200 to avoid interference with the outer diameter of the button 100, and extends to a position at or near the interface between the first post 202 and base 200 to avoid interference with the lower end of the button 100. The cannula spring 300 is then extended from the groove or slot 208 in the first post 202, along a surface of the base 200, toward the second post 204.

At the second post 204, the cannula spring 300 is wound to encircle the second post 204, thereby forming coils of the retraction spring portion 306. Although 4 coils of the retraction spring portion 306 are shown, embodiments of the present invention are not limited thereto. The retraction spring portion 306 of the cannula spring 300 is disposed around the second post 204 to a position at or near the top of the second post 204. A clearance space is provided between the coils of the retraction spring portion 306 of the cannula spring 300 and an inside diameter of the first projection 102 of the button 100. The cannula spring 300 is then extended through a groove or slot 210 in the second post 204 of the base 200, and extends through a groove or slot 110 of the button 100 toward a position above the septum 226.

Once above the septum 226, the cannula spring 300 is angled to extend through the septum 226, catheter 228 and catheter securing wedge 230, thereby forming the introducer needle portion 302. The distal end of the introducer needle portion 302 can be sharpened, beveled or blunt as required by the application.

Figure 4:
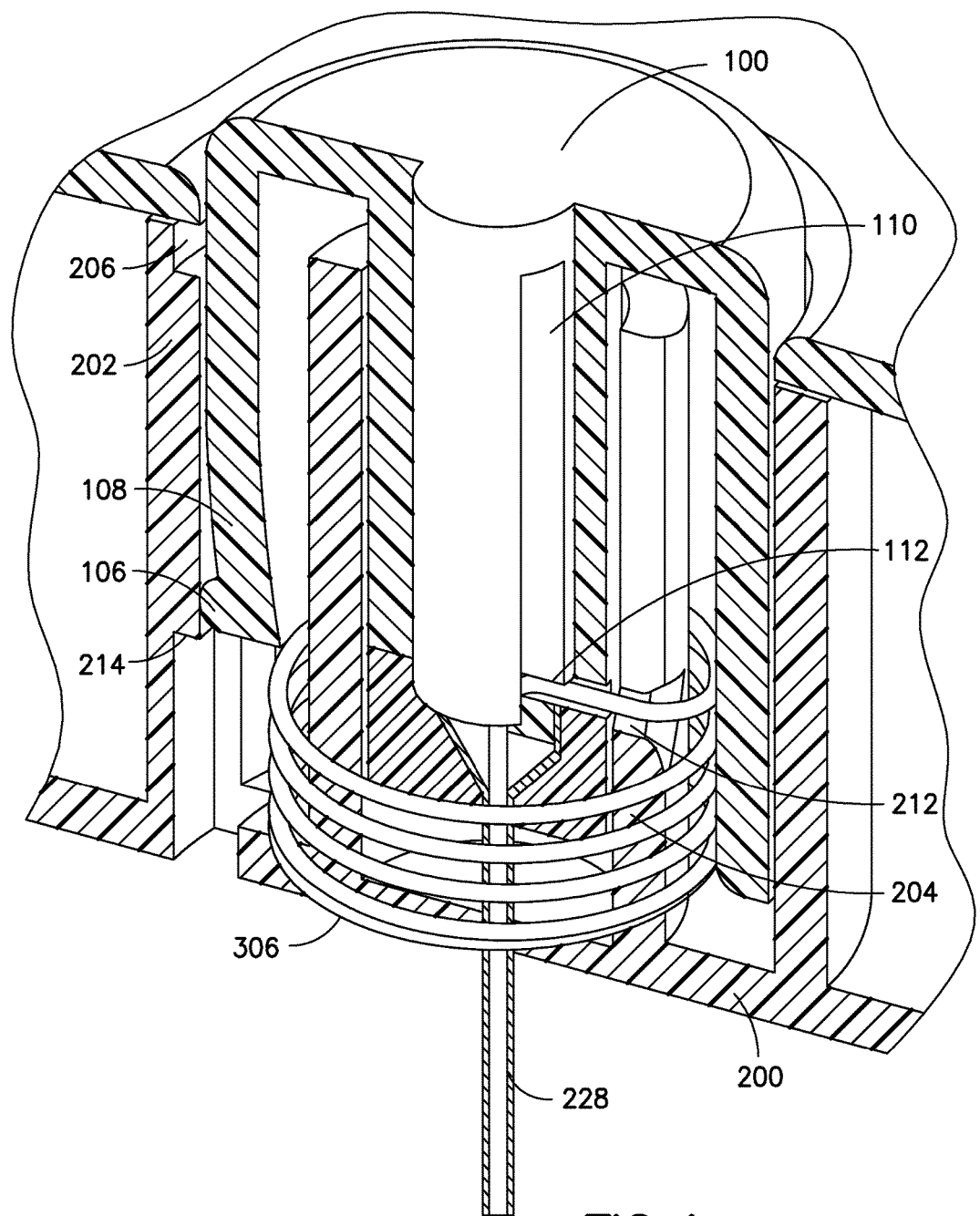
FIG. 4 is an enlarged cross-sectional view of the exemplary infusion device nearing the completion of activation in accordance with an embodiment of the present invention.

At the point where the cannula spring 300 extends through the slot 110 of the button 100, it is releasably captured by a step detent 112 of the slot 110 of the button 100 as shown in FIG. 4. In doing so, as the button 100 is pressed downward, the cannula spring 300 passing through the button 100 is pressed downward by the step detent 112 of the slot 110, thereby activating the coils of the retraction spring portion 306. As described in greater detail below, upon complete activation, the cannula spring 300 is released from the step detent 112 and displaced into the slot 110 of the button 100, such that the activated coils of the retraction spring portion 306 are free to expand through the slot 110 of the button 100 and retract the introducer needle portion 302 even while the button 100 is held in the activated position.

FIG. 3 shows the device as the button 100 is just being forced pass the detents 106 and 206. As noted above, the sudden release of the projecting detent 106 from the stepped detent 206 is configured to occur once a desired amount of activation force has been applied to the button 100. As the button 100 begins to travel, the second projection 104 of the button 100 slidably moves the septum 226, catheter 228 and catheter securing wedge 230. It is also at this time when the step detent 112 of the button 100 begins to force the cannula spring 300 downward by pushing on the topmost coil of the retraction spring portion 306, thereby simultaneously pushing the introducer needle portion 302 downward and activating the coils of the retraction spring portion 306. The sudden release of the projecting detent 106 from the stepped detent 206 is configured to allow the button 100 to rapidly and smoothly push the introducer needle portion 302 and plastic catheter 228 downward and into the body of the user with minimal pain and discomfort.

As the button 100 continues to be pressed downward and the introducer needle portion 302 of the cannula spring 300 reaches the desired depth, the topmost coil of the cannula spring 300 hits an incline or ramp 212 in the second post 204 of the base 200 which that forces the cannula spring 300 to rotate slightly, as indicated in FIG. 4. FIG. 4 is an enlarged cross-sectional view of the exemplary infusion device nearing the end of activation in accordance with an embodiment of the present invention. As the cannula spring 300 rotates, it will no longer be acted upon by the step detent 112 of the button 100, and is released into the slot 110 of the button 100. This allows the activated coils of the retraction spring portion 306 of the cannula spring 300 to expand into the slot 110 and retract the introducer needle portion 302 from the body of the user as shown in FIG. 5.

As noted above, once the desired amount of activation force, speed, smoothness and angle has been applied to the button 100, the rounded detent 106 and member 108 are deflected and are released from the engagement with the stepped detent 206 of the post 202 of the base 200. The button 100 is then free to be pressed downward against the resistance of the deflected detent 106 and member 108 resiliently urged into contact with the inner diameter of the post 202 of the base 200. At a complete down position, the rounded, projecting detent 106 is captured within a stepped detent 214 of the post 202 of the base 200. Therefore, the projecting detent 106 and thereby, the button 100, is held in the down and pressed position by the engagement between the projecting detent 106 and the stepped detent 214 as shown in FIG. 5. Further, the septum 226, catheter 228 and catheter securing wedge 230 are held in the down and pressed position by the engagement between the projecting detent 106 and the stepped detent 214.

Figure 5:
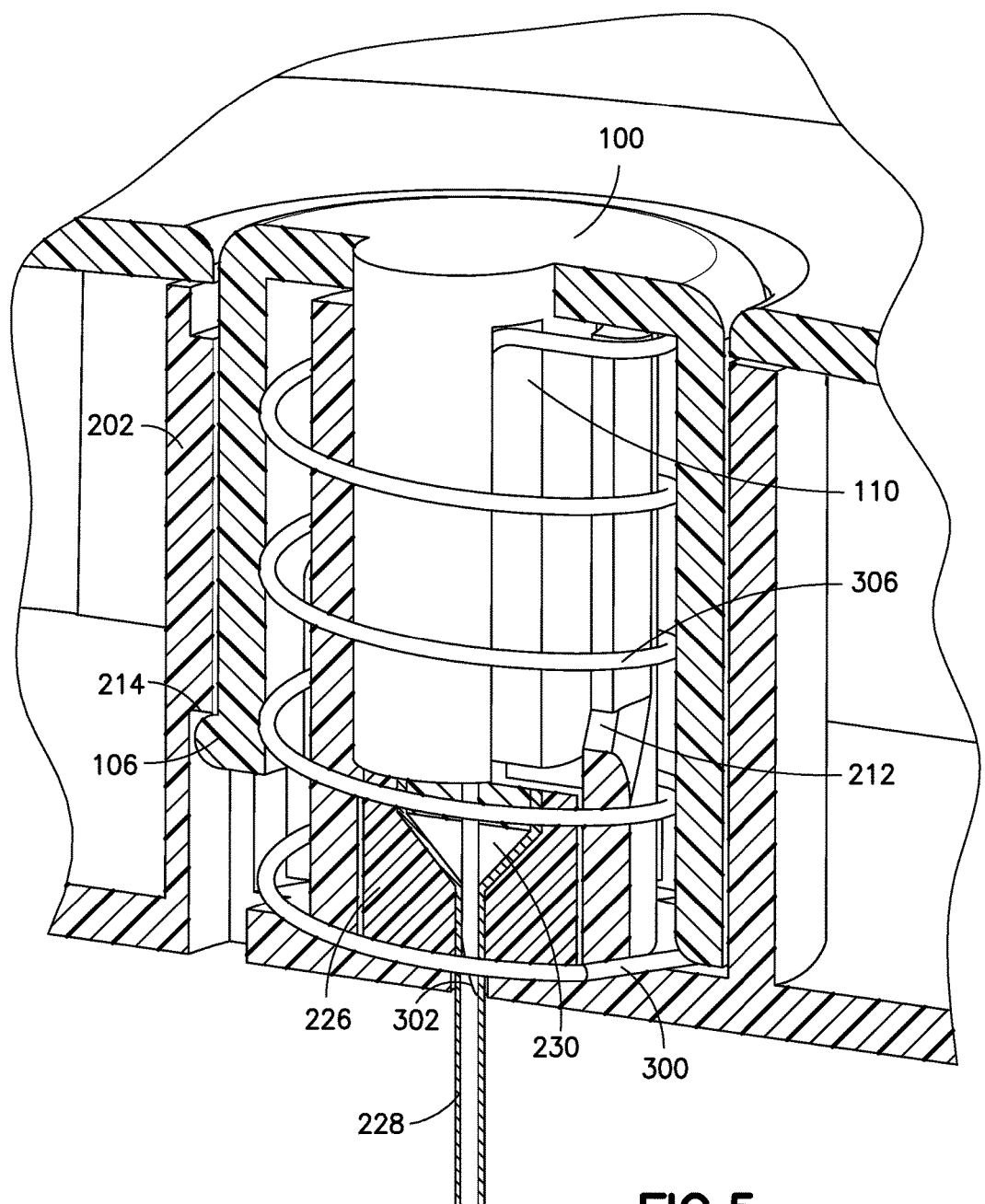
FIG. 5 is an enlarged cross-sectional view of the exemplary infusion device of FIG. 1B after activation in accordance with an embodiment of the present invention.

FIG. 5 is an enlarged cross-sectional view of the exemplary infusion device of FIG. 1B after activation in accordance with an embodiment of the present invention. FIG. 5 shows the spring 300 fully expanded, with the introducer needle portion 302 retracted from the body of the user, wherein the distal end or tip of the introducer needle portion 302 is still inside the catheter 228, providing a sealed and uninterrupted fluid path.

In the exemplary embodiments, the introducer needle, retraction spring and fluid path are all inherently part of the single piece of cannula tubing, and no flexible tubing is required. Flexible tubing is used in other designs so the fluid path can move along with the motion of the introducer needle and/or catheter. Such flexible tubing requires significant space within the infusion device to keep it from being pinched or kinked. Such flexible tubing can also be difficult to handle during production because it lacks any rigid shape. Further, since the introducer needle, retraction spring and fluid path are all inherently part of the single piece of cannula tubing, the part count of the device is lower and the overall size of the device is smaller than conventional devices. Accordingly, exemplary embodiments of the present invention keep part production costs low, as well as simplify assembly of the infusion device.

The cannula spring 300 requires a very small notch or hole in order to pass through the water tight seal provided by the walls of the post 202. That is, the post 202 into which water from a shower or swimming is free to enter through the catheter exit hole or from the button hole in the housing top, is hermetically sealed with laser welding or gluing, thereby protecting the remaining content of the device housing 10, such as content of the electronic/pump compartments of the device. The outer walls of the insertion mechanism also provide a water tight seal. Any notch or hole can be easily filled with glue around the cannula spring 300 in order to provide and maintain the desired water tight seal.

In the exemplary embodiments of the present invention, a single piece of hollow cannula tubing is wound, bent and sharpened into a shape which allows it to operate as an introducer needle, retraction spring and fluid path. The button of the infusion device upon activation, is used to optimally insert the introducer needle portion of the cannula spring and a soft catheter, activate the retraction spring portion the cannula spring, and once the introducer needle portion and catheter have been fully inserted, release the retraction spring portion the cannula spring such that the introducer needle portion automatically retracts, leaving the catheter in the body of the user. An end of the introducer needle portion of the cannula spring remains in the inserted catheter to provide an uninterrupted fluid path.

Figure 6:
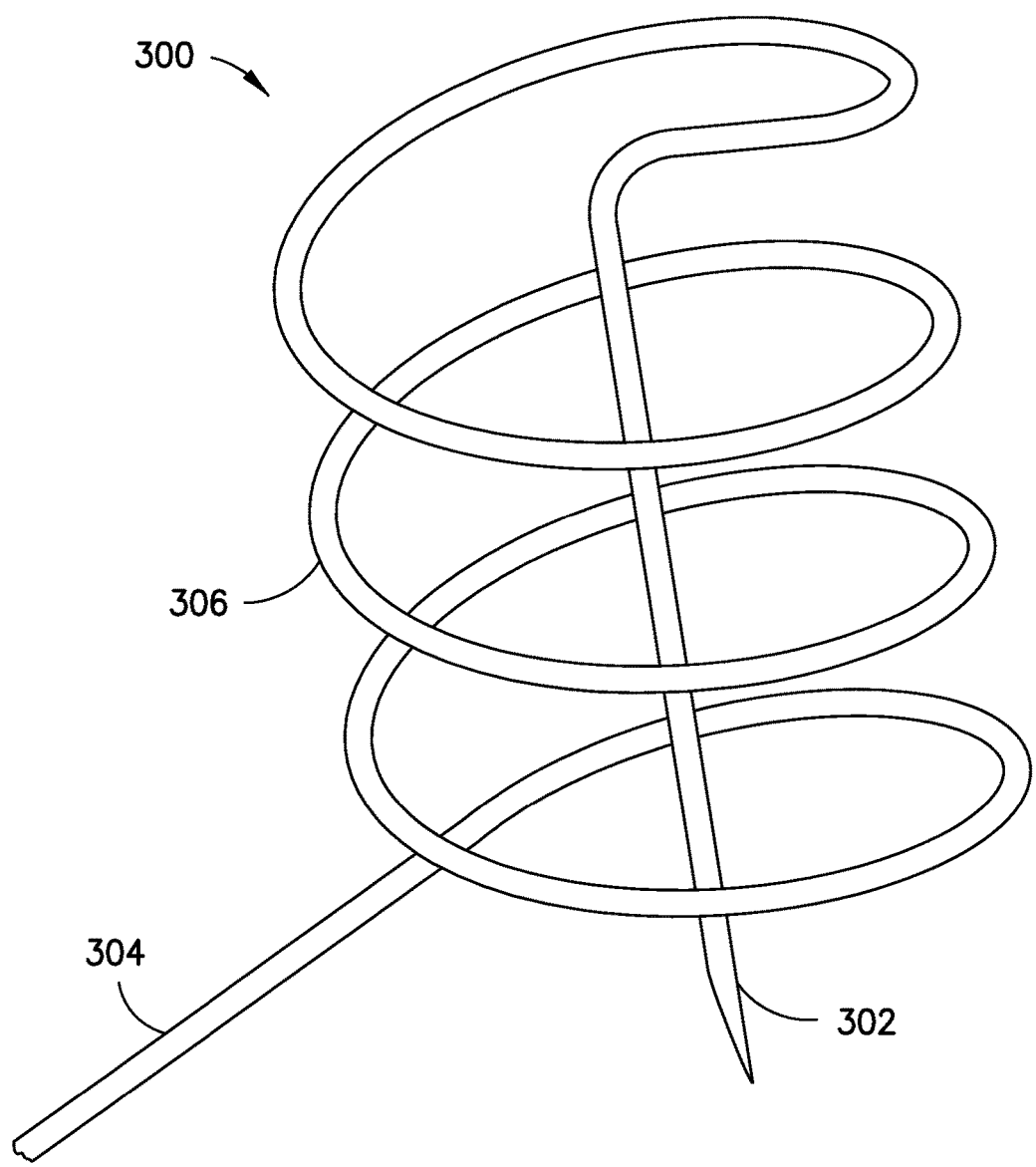
FIG. 6 is an enlarged perspective view of an exemplary cannula spring of the exemplary infusion device in accordance with an embodiment of the present invention.

The exemplary embodiments of the present invention are possible due to one or more shared technical features of the elements therein. Accordingly, an object of the present invention is to provide a cannula spring which functions as an introducer needle, spring, and fluid path. An example of such a cannula spring 300 as described in regard to FIGS. 1-5, is shown in FIG. 6. FIG. 6 is an enlarged perspective view of an exemplary cannula spring in accordance with an embodiment of the present invention.

In regard to FIG. 6, the cannula spring 300 is shown removed from the device to show the end 302 of the tubing used as an introducer needle portion and the other end 304 used to connect to a fluid path, and a middle portion 306 coiled to form a spring portion. In the embodiment shown in FIG. 6, the long tail of the cannula spring 300 can be bent in any desired shape or contour to mate with any of a reservoir, pump or other supply. A diameter of the cannulae spring 300 can be substantially the same as the diameter required for an introducer needle, and can be substantially the same as the diameter required for spring wire. Where cannulae of an infusion device are constructed using metal or plastic, such as 304 stainless steel, such materials can also be used to construct springs and fluid paths. A diameter of such cannulae can be substantially the same as a diameter of spring wire, such as that used for insertion, retraction, or safety springs in an infusion device. The exemplary cannula spring 300 can be formed from a single continuous piece of steel tubing with diameter of about 0.0103 inches (0.26 mm), which shares the same diameter as a 31G steel cannula. 31 G is the most common gauge for steel in-dwelling patient cannula, such as those available from V-Go™ and Orbit™. The exemplary cannula spring 300 formed from the steel tubing with diameter of about 0.0103 inches (0.26 mm) in this manner exerts a force of about 0.35 lbs (1.56 N) at the beginning of retraction and about 0.17 lbs (0.76 N) at the end of the retraction. The spring force is proportional to the inverse of the polar moment of inertia which, for an annulus, is noted below in Equation (1), repeated below.

$$\pi/2(\text{outer radius}^4 - \text{inner radius}^4) \qquad \text{Equation (1)}$$

If a regular wall thickness cannula, that is, a cannula with a wall thickness of about 0.003 inches (0.076 mm), is used to make the exemplary cannula spring 300, the spring force would only drop by about 6% compared to the retraction spring formed from the steel tubing with a diameter of about 0.00103 inches (0.26 mm). This reduced spring force would still give the necessary retraction force. Accordingly, an fluid infusion device can be provided with a cannula spring which functions as an introducer needle, a retraction return spring, and a fluid path, that facilitates insertion of the in-dwelling or soft catheter and if required, retract the introducer needle, while reducing the number of components required for the construction and use of the infusion device.

Figure 7:
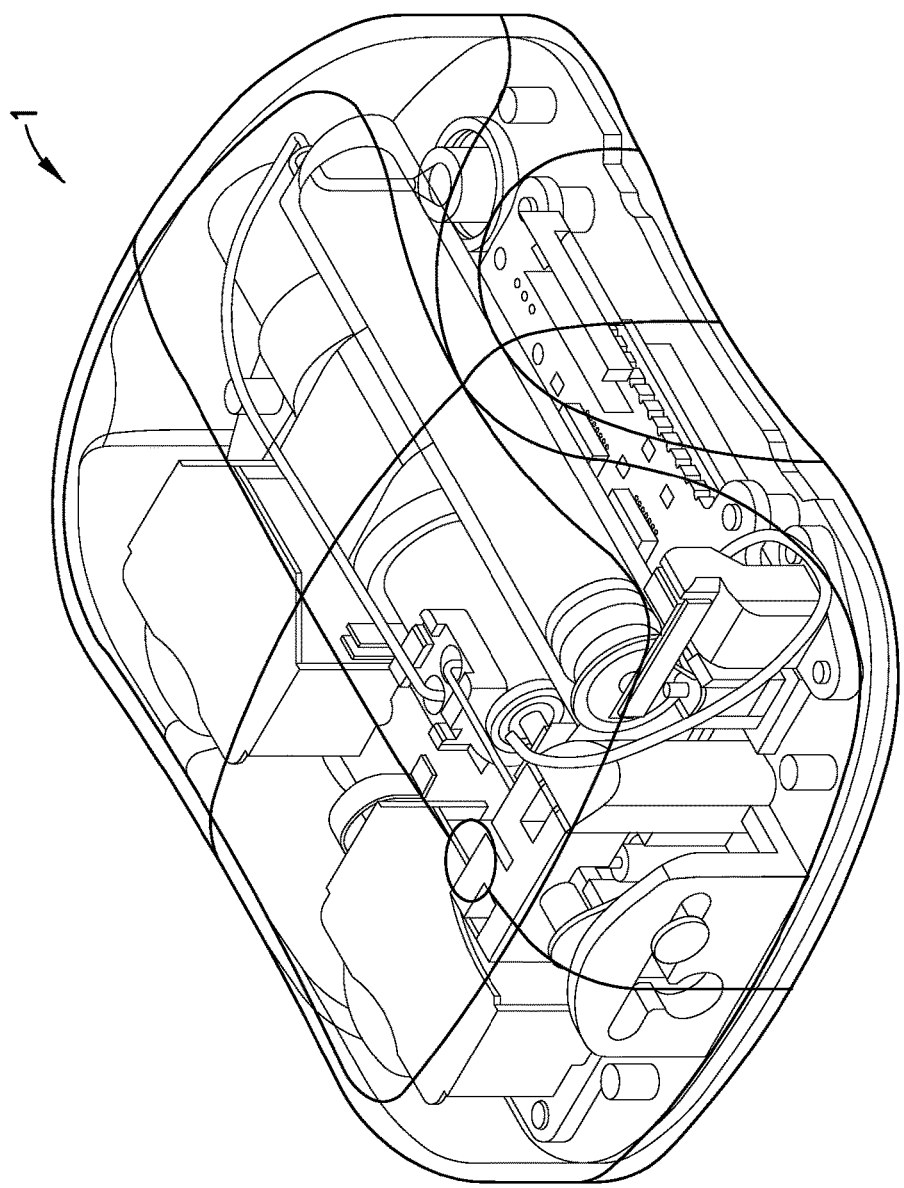
FIG. 7 is a perspective view of a patch pump incorporating a low-profile cannula insertion device, illustrated with a see-through cover for clarity.
Figure 8:
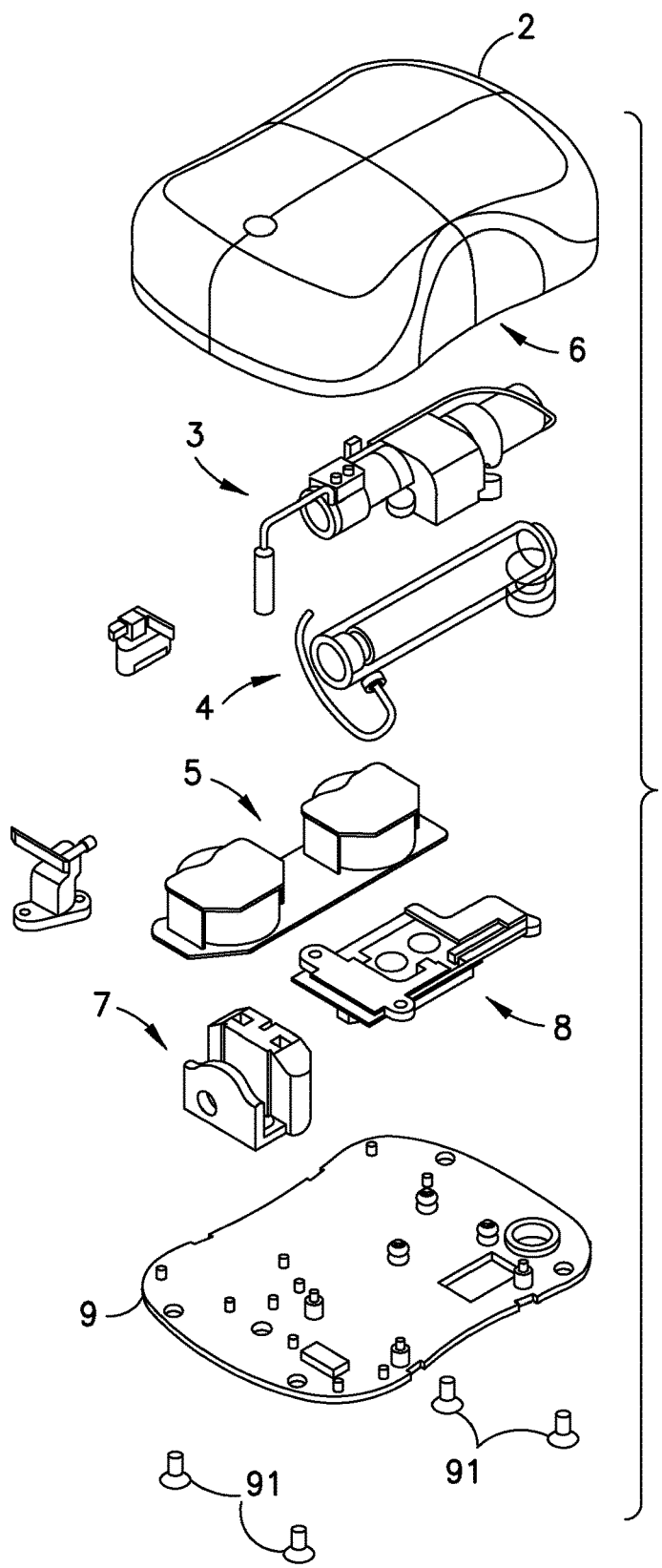
FIG. 8 is an exploded view of the various components of the patch pump of FIG. 7, illustrated with a cover.

In the above embodiments, a patch pump can be provided with one or more of the described features. FIG. 7 is a perspective view of an exemplary embodiment of a patch pump 1 according to an exemplary embodiment of the invention. The patch pump 1 is illustrated with a see-through cover for clarity and illustrates various components that are assembled to form the patch pump 1. FIG. 8 is an exploded view of the various components of the patch pump of FIG. 7, illustrated with a solid cover 2. The various components of the patch pump 1 may include: a reservoir 4 for storing fluid such as insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

As noted above, it should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the fluid flow path to deliver fluid until the infusion is finished. For discussion purposes, the fluid is an insulin fluid, but embodiments are not limited thereto. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 9:
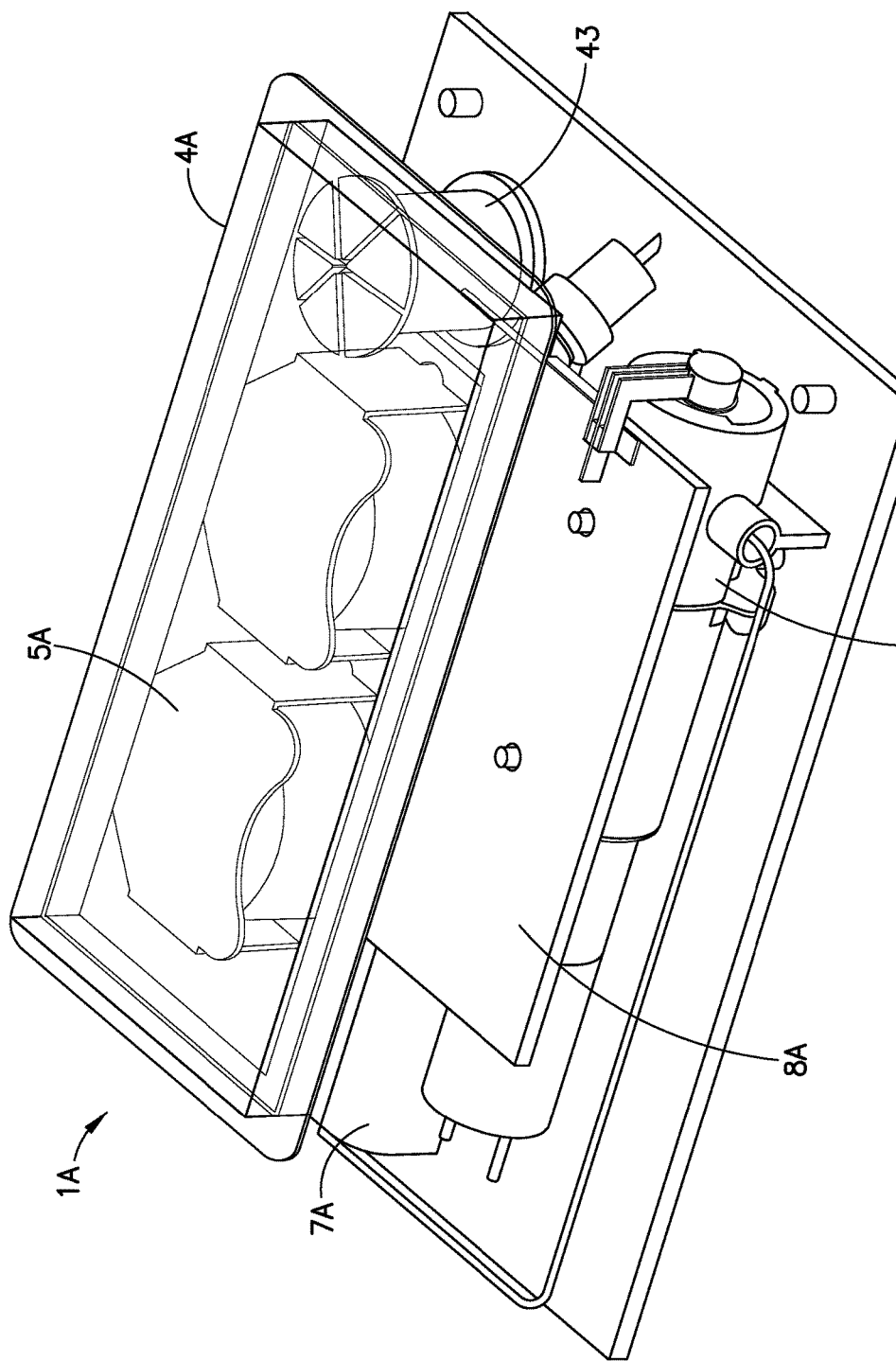
FIG. 9 is a perspective view of an alternative design for a patch pump having a flexible reservoir, illustrated without a cover.

FIG. 9 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 10:
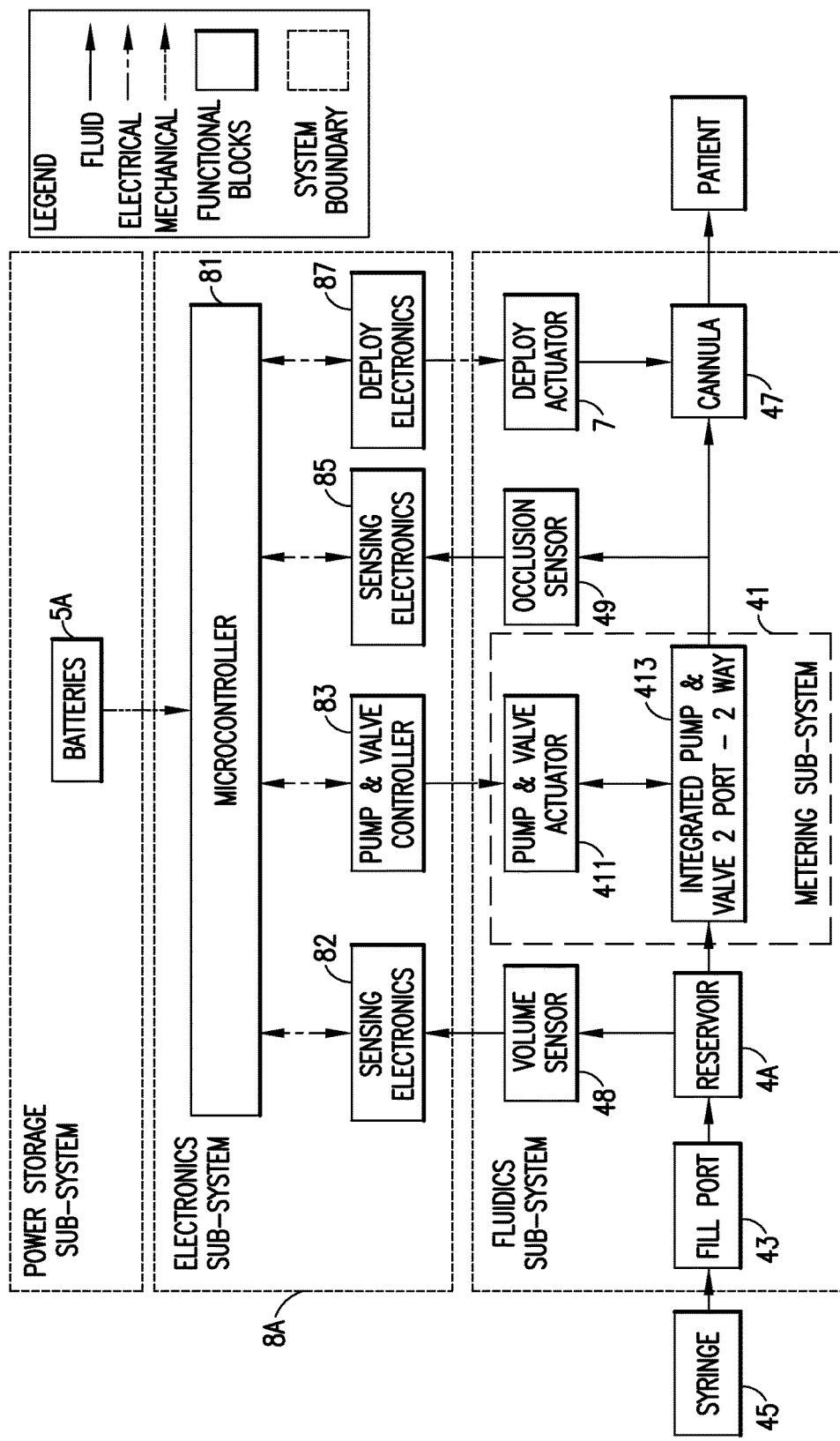
FIG. 10 is a patch-pump fluidic architecture and metering sub-system diagram of the patch pump of FIG. 9.

FIG. 10 is a patch-pump fluidic architecture and metering sub-system diagram of the patch pump 1A of FIG. 9. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87 that control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 7 and 8 is the same or similar to that which is illustrated in FIG. 10.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and their equivalents.

The invention claimed is:

1. An fluid infusion device, comprising:
 a body, comprising an activation button;
 a base, slidably receiving said activation button; and
 a hollow cannula tubing member comprising an introducer needle portion and a spring portion wherein the introducer needle portion and the spring portion are integrally formed,
 wherein said activation button is slidable to insert said introducer needle portion of said hollow cannula tubing member into a body of a user and activate said spring portion of said hollow cannula tubing member, and upon insertion,
 release said spring portion of said hollow cannula tubing member to retract said introducer needle portion of said hollow cannula tubing member from said body of said user;
 further comprising:
 a catheter for insertion by said introducer needle portion of said hollow cannula tubing member into said body of said user,
 wherein an end of said introducer needle portion of said hollow cannula tubing member remains in fluid communication with said catheter in said body of said user to comprise an uninterrupted fluid path.

2. The fluid infusion device of claim 1, wherein said hollow cannula tubing member further comprises a fluid path portion.

3. The fluid infusion device of claim 1, further comprising:
 a detent disposed on said activation button to releasably engage said base, wherein said detent is configured to secure said button in a first position until an activation force applied to said button exceeds a threshold.

4. The fluid infusion device of claim 1, further comprising:
 a detent disposed on said activation button to releasably engage said base, wherein said detent is configured to secure said button in a second position after an activation force has been applied to said button.

5. An fluid infusion device, having a body and an activation button, and a base slidably receiving said activation button, comprising:
   a hollow cannula tubing member comprising an introducer needle portion and a spring portion, wherein the introducer needle portion and the spring portion are integrally formed, wherein said introducer needle portion of said hollow cannula tubing member is moveable in a first direction as said spring portion of said hollow cannula tubing member is activated, and
   said spring portion of said hollow cannula tubing member is expandable to move said introducer needle portion of said tubing in a second direction as said spring portion of said hollow cannula tubing member is expanded;
   wherein said hollow cannula tubing member remains in fluid communication with a catheter inserted into the body of a user by the introducer needle portion.

6. The fluid infusion device of claim 5, wherein said hollow cannula tubing member further comprises a fluid path portion.

7. An fluid infusion device, having a body and an activation button, and a base slidably receiving said activation button, comprising:
   a hollow cannula tubing member comprising an introducer needle portion and a spring portion, wherein the introducer needle portion and the spring portion are integrally formed, wherein said introducer needle portion of said hollow cannula tubing member is moveable in a first direction as said spring portion of said hollow cannula tubing member is activated, and
   said spring portion of said hollow cannula tubing member is expandable to move said introducer needle portion of said hollow cannula tubing member in a second direction as said spring portion of said hollow cannula tubing member is expanded; and
   a catheter disposed upon said introducer needle portion of said hollow cannula tubing member for insertion by said introducer needle portion of said hollow cannula tubing member into a body of a user.

8. The fluid infusion device of claim 7, wherein an end of said introducer needle portion of said hollow cannula tubing member remains in fluid communication with said catheter in said body of said user to comprise an uninterrupted fluid path.

9. The fluid infusion device of claim 7, wherein said hollow cannula tubing member further comprises a fluid path portion.

* * * * *